United States Patent [19]
Repke

[11] 3,993,820
[45] Nov. 23, 1976

[54] NON-WOVEN PRODUCT

[75] Inventor: Virginia L. Repke, Oak Forest, Ill.

[73] Assignee: Johnson & Johnson, New Brunswick, N.J.

[22] Filed: July 1, 1975

[21] Appl. No.: 592,483

Related U.S. Application Data

[63] Continuation of Ser. No. 376,193, July 2, 1973, abandoned, which is a continuation-in-part of Ser. No. 187,472, Oct. 7, 1971, abandoned.

[52] U.S. Cl. ............................ 428/167; 428/171; 428/296; 128/290 R; 128/290 P
[51] Int. Cl.² ........................................ A61F 13/18
[58] Field of Search ............ 128/155, 156, 290 R, 128/284, 296; 428/156, 167, 170, 171, 172

[56] References Cited
UNITED STATES PATENTS

| | | | |
|---|---|---|---|
| 2,952,260 | 9/1960 | Burgeni | 128/290 |
| 2,955,641 | 10/1960 | Burgeni | 128/290 |
| 3,017,304 | 1/1962 | Burgeni | 128/290 |
| 3,060,936 | 10/1962 | Burgeni | 128/290 |
| 3,343,543 | 9/1967 | Glassman | 128/290 |
| 3,371,667 | 3/1969 | Morse | 128/290 |
| 3,403,681 | 10/1968 | Hoey et al. | 128/290 |
| 3,420,235 | 1/1969 | Harman | 128/290 |
| 3,494,362 | 2/1970 | Burgeni | 128/290 |
| 3,545,441 | 12/1970 | Graydahl | 128/284 |
| 3,707,430 | 12/1972 | Costanza et al. | 128/290 |

*Primary Examiner*—Ralph S. Kendall

[57] ABSTRACT

A fluid absorbing and storing structure comprising a highly porous, loosely compacted cellulosic fibrous batt, and integral therewith, a continuous paper-like, densified, cellulosic fibrous layer having selectively thickened portions for rapidly directing fluid away from an initially wetted area. The major unthickened portion of the paper-like, densified layer merges with the loosely compacted batt at a generally planar interface, and the thickened portions extend through the plane of the interface and into the loosely compacted batt to give the structure increased strength. The batt may be contoured to provide increased fluid storage capacity in the central area of the structure. A marginal fluid boundary of loosely compacted cellulosic fibers may be provided to aid in containing fluid within the structure. Further, end edge boundaries in the form of thickened, densified transverse lines near the ends of the densified layer may be included to provide a means for transferring fluid flow laterally to adjacent longitudinal thickened portions. The thickened portions may be coherent and unitary, or may include substantially fiber-free voids surrounded by fibrous strata.

17 Claims, 28 Drawing Figures

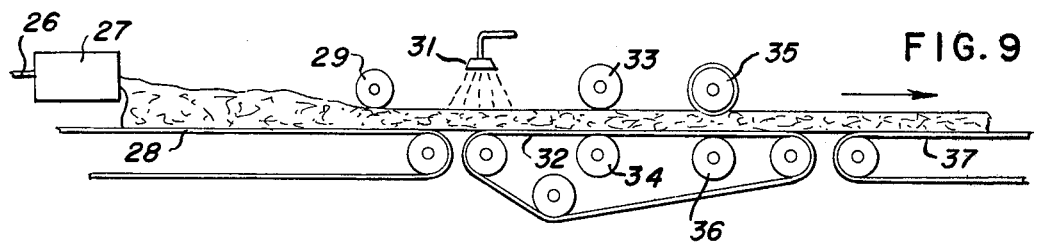
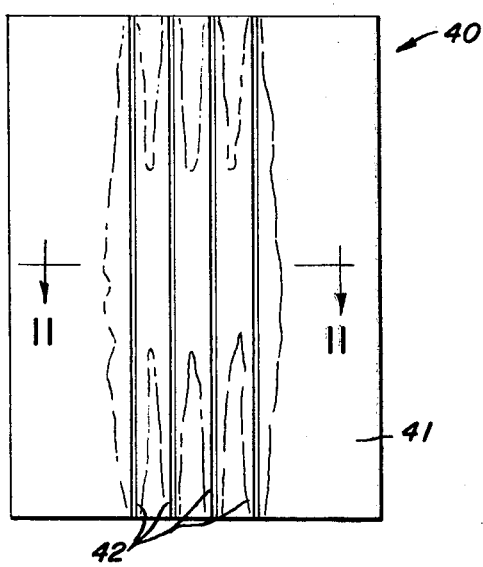
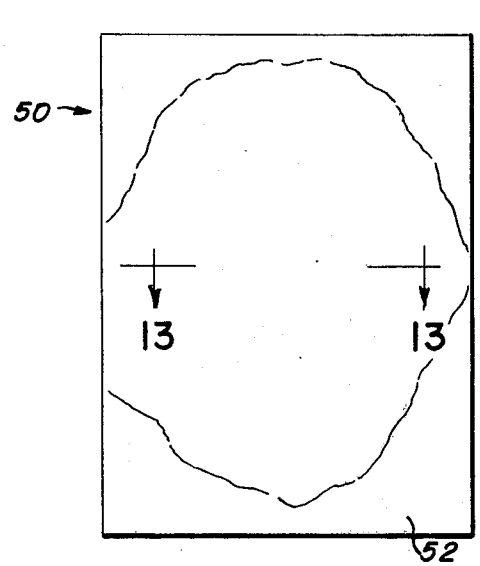
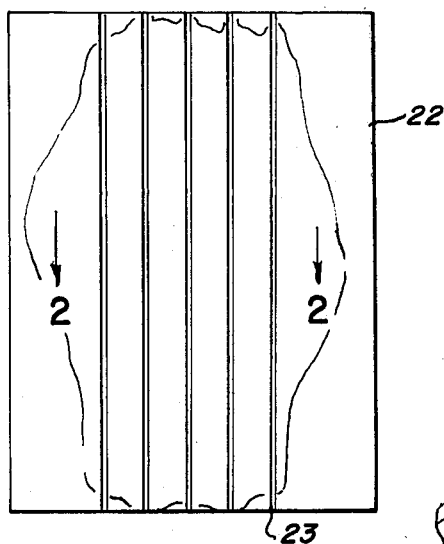
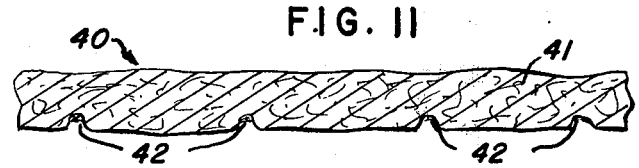
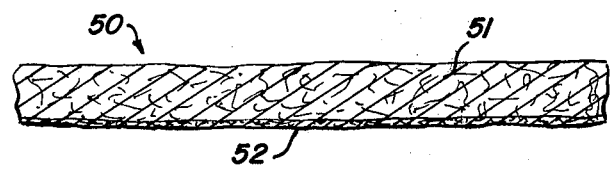
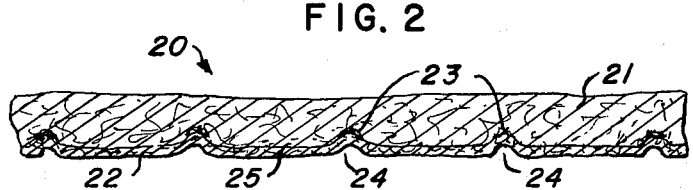

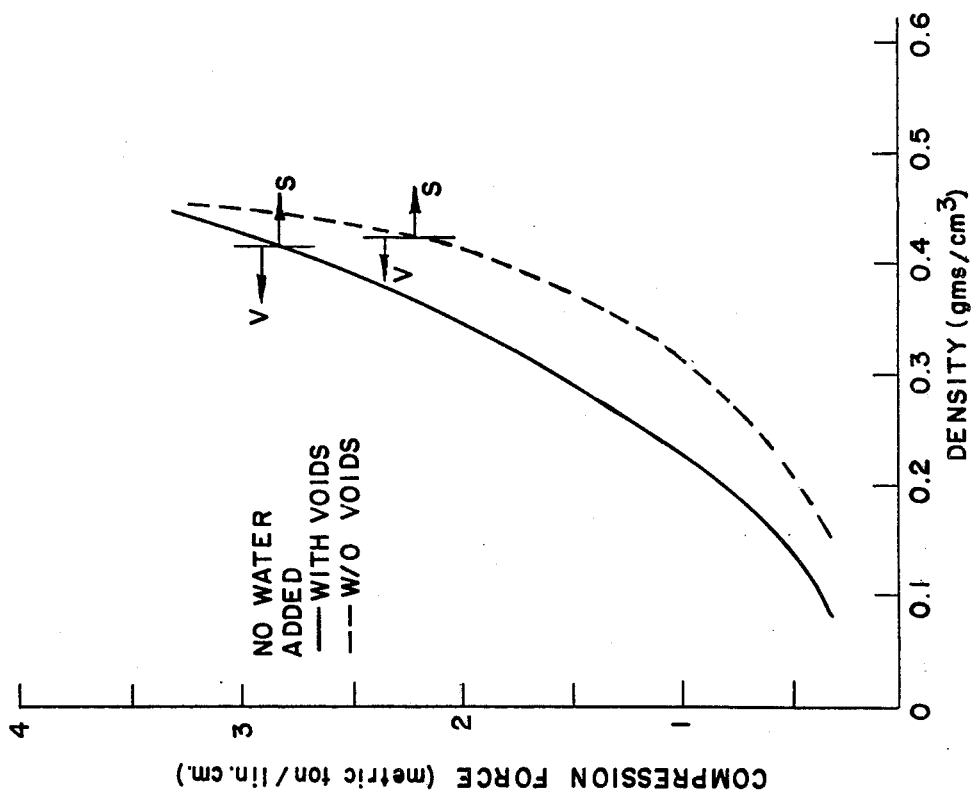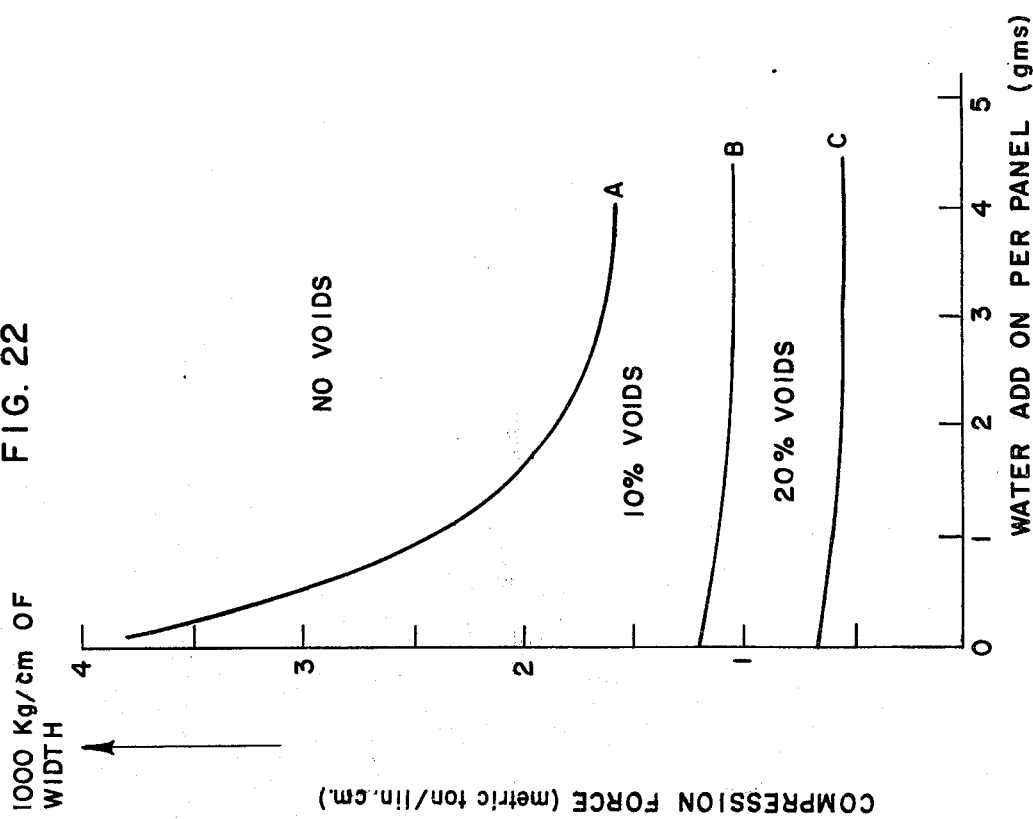

NON-WOVEN PRODUCT

CROSS-REFERENCE TO RELATED APPLICATIONS

This application is a continuation application of my application Ser. No. 376,193, filed July 2, 1973, now abandoned, which in turn was a continuation-in-part application of my application Ser. No. 187,472, filed Oct. 7, 1971, now abandoned.

BACKGROUND OF THE INVENTION

The present invention relates generally to absorbent products, and more particularly to absorbent products comprising a highly porous, loosely compacted cellulosic fibrous batt having a paper-like, densified, cellulosic fibrous layer formed integrally therewith. Absorbent structures of the above described type have found widespread commercial utility in products intended to absorb body fluids, and reference may be made to U.S. Pat. Nos. 2,952,260; 2,955,641; 3,017,304; 3,060,936 and 3,494,362 for a more complete description of the prior art structures, the methods of producing the structures, and the various end products in which the structures may be used. The prior art structures mentioned above have met with widespread commercial success, particularly because the densified layer provides increased capillary forces which cause the liquid to flow preferentially into the densified layer, and to spread outwardly in the densified layer at a relatively rapid rate, and also because of the increased structural strength that is imparted to the absorbent product by the densified layer.

The above mentioned prior art absorbent structures may be classified in two groups, viz., those wherein the paper-like, densified layer extends continuously over a given area of the absorbent structure, and those wherein the paper-like, densified layer is discontinuous and arranged in a preselected geometric pattern. The advantage of the absorbent structures within the latter group is the ability to provide directionalized fluid flow, i.e., the fluid tends to flow in the direction of the densified portions, as opposed to flowing into the loosely compacted portions of the absorbent structure. The ability to control the direction of fluid flow is of particular importance in a product of unequal dimension, such as a sanitary napkin, which is substantially longer than it is wide.

Thus, in such an end product, by utilizing an absorbent structure wherein the spaced densified portions extend in a lengthwise direction, the fluid flows preferentially along the densified portions to spread out longitudinally within the product before spreading laterally and striking through at the side edges thereof. While absorbent products having spaced densified portions provide increased ability to control and direct the flow of fluid, as opposed to a continuous paper-like, densified layer wherein the fluid flow is substantially equal in all directions, such structures have a reduced volumetric fluid storage capacity in the densified portions and somewhat reduced overall structural integrity, as compared to comparable structures having a continuous paper-like, densified layer. Furthermore, because the spaced densified portions of the structure are separated by loosely compacted batt portions having limited wickability, the flow rate in the densified portions is far greater than the rate of spread, with the result that fluid often reaches the ends of the densified portions before it spreads outwardly into previously unwet portions of the absorbent structure. This, of course, results in fluid leakage at the ends of the absorbent structure.

In absorbent structures including a continuous densified layer of uniform thickness, because of the equal flow rate in all directions, in rectangular products the fluid often migrates to the side edges of the densified layer before it reaches the longitudinal edges thereof, with resultant fluid leakage at the sides of the product. Thus, both types of prior art absorbent structures have certain limitations.

SUMMARY OF THE INVENTION

The present invention represents a significant improvement upon absorbent structures of the above described type, by providing a highly porous, loosely compacted fibrous cellulosic batt with an integral, continuous paper-like, densified, cellulosic fibrous layer which, in selected areas, is thickened with additional densified cellulosic fibrous material. The thickened and unthickened portions of the densified layer portion of the absorbent structure cooperate with one another to provide for increased flow of fluid within the densified portions of the absorbent structure by reason of a greater cross sectional area therewithin, thereby tending to cause a greater amount of the fluid striking the loosely compacted batt portion of the absorbent structure to flow preferentially into the densified layer portion and then throughout the densified layer portion toward its outer edges.

The spaced thickened portions of the densified layer provide for an increased volumetric flow rate of fluid (as compared to the unthickened portions of the densified layer) and thus aid in rapidly transporting an increased volume of fluid into remote areas of the densified layer portion before fluid flows back into the loosely compacted fibrous batt portion of the absorbent structure. The thickened densified portions thereby make possible the utilization of substantially the entire absorbent capacity of the densified layer portion, i.e., the fluid is transported to both the side and longitudinal edges of the batt portion of the absorbent structure, before the fluid flows back into the loosely compacted batt portion of the absorbent structure.

The unthickened portions of the densified layer portion function as bridging regions which transport fluid from one thickened densified portion to another at a relatively rapid rate, although the volume of fluid that spreads from one thickened portion to another is less than the volume of fluid that is transported along the thickened portions themselves in a given period of time. However, as the spreading fluid reaches unwetted thickened densified portions, the increased volumetric flow capacity resulting from these thickened portions provides a means for rapidly taking up the fluid and causing it to spread out rapidly along the thickened portions and into previously unwet densified layer portions of the absorbent structure. Thus, by virtue of having a continuous paper-like densified portion with selectively thickened regions therein, a medium is provided for preferentially drawing fluid away from the loosely compacted batt of the absorbent structure, while enabling the fluid to spread outwardly in the entire densified layer at a relatively rapid rate by virtue of the increased flow rate along the thickened portions as well as from one thickened portion of the densified layer to another.

In one embodiment of the invention, the thickened portions of the densified layer are provided by spaced, parallel strips or lines of densified fibrous material that extend lengthwise of the structure. When the absorbent structure is wetted in the central region of the batt portion and the fluid flows into the densified layer of the absorbent structure, the thickened portions in that region function to rapidly transport the fluid lengthwise of the structure away from the initially wetted region, while the densified bridging portions between the thickened portions cause the fluid to spread laterally outwardly at a rapid rate, thus causing the fluid to encounter additional thickened portions of densified material, with resulting increased longitudinal flow. It will be appreciated with the above described type of structure, an arrangement is provided that will rapidly draw fluid away from an initially wetted region, and cause it to pread out and utilize the absorptive capacity of the entire densified layer portion prior to its flow back into the loosely compacted batt of the absorbent structure.

The above-mentioned densified strips or lines need not be continuous to provide the improved fluid directing function, and it has been found that lines formed of relatively closely spaced strips or sections have also functioned satisfactorily. Indeed, with the latter arrangement stiffness in the direction of the densified lines is minimized and an extremely conformably absorbent structure is produced, which at the same time retains the desired fluid directing characteristics.

The cross-sectional area of the densified layer that includes the thickened portions is greater than the cross-sectional area of the prior art structures including a continuous paper-like densified layer with no thickened portions, or a prior art structure including spaced densified zones, with the result that an increased volumetric storage capacity is provided within the densified layer portion and, of course, within the absorbent structure.

In another embodiment of the invention, the thickened portions of the densified layer are provided by first and second groups of spaced, parallel strips or zones, with the strips or zones being disposed at an angle with respect to one another, and with respect to the length of the absorbent structure, to provide a diamond-like grid pattern of unthickened densified portions throughout the absorbent structure. It will be appreciated that with this latter structure, by virtue of the multiple intersections between the thickened densified portions, the spread of fluid outwardly from the initially wetted region of the densified portion is significantly increased. Since in this embodiment the thickened densified portions extend to the side margins and corners of the absorbent structure, the fluid is effectively and rapidly transported to virtually all portions of the densified layer portion.

In all of the embodiments described above, the unthickened portion of the densified layer merges with the loosely compacted batt portion of the absorbent structure at a generally planar interface. The thickened portions of the densified layer extend beyond the said interface and into the interior of the batt portion to provide a three-dimensional strengthening effect which markedly improves the structural integrity of the absorbent product. The increased strength imparted to the absorbent structure is important not only in use when the structure resists the stress imparted by the absorbed liquid, but it is also of significance during the manufacture of the absorbent structure, since it improves the handling capabilities enabling the absorbent structure to be produced without difficulty by high-speed machinery.

Furthermore, since the thickened densified portions may be extended into the batt portion of the absorbent structure, they may be positioned closer to the opposite face of the structure and will be struck by fluid more quickly than the fluid would reach a densified layer of uniform thickness. As a result, the spread of fluid is initiated more quickly. The thickened densified portions may extend through the entire cross-sectional thickness of the batt portion, which gives the batt a marked increase in structural integrity. With this latter structure, sufficient stability is imparted to the batt to permit the use of lower densities in the loosely compacted portion thereof than heretofore thought posssible. This, of course, enhances the drape and conformability of the absorbent structure. Thus the absorbent structure of the present invention has all of the advantages of the prior art structures disclosed in the abovementioned patents, or having improved strength, increased fluid storage capacity, and improved fluid directing and absorbing properties.

The batt portion of the absorbent structure of the present invention may also be heavier, i.e., more dense, in the central region than at the side marginal edges. When the structure is utilized in an environment in which weight is likely to be concentrated at its central region, such as in a disposable diaper or in a bed pad, the heavier center tends to concentrate a large volume of fluid in the central region and thereby minimize leakage at the sides of the absorbent structure. In this embodiment, when a batt is of a given absorptive capacity, and has a given number of fibers, making the central region heavier inherently makes the side portions lighter than would be obtained in a batt of uniform density and thickness. The central region of the batt portion is preferably thicker than the side marginal edges thereof, and the relatively thin, low density side marginal edges may, for some end uses such as sanitary napkins and disposable diapers, enable the absorbent structure to be more readily conformed during use.

In a slightly modified form of the above-described embodiments the densified layer does not extend to the side edges of the absorbent structure, but instead, the loosely compacted batt portion extends outwardly of the marginal side edges of the densified layer portion. In this embodiment the less dense batt portion, which has reduced wettability, acts as a barrier to block fluid from spreading or migrating beyond the side edges of the absorbent structure.

The densified layer may also include (in addition to longitudinal thickened lines) transverse thickened lines close to the end edges of the absorbent structure. These transverse thickened lines act to direct fluid transversely to adjacent longitudinal thickened lines and adjacent portions of the densified layer and thereby direct fluid back along these adjacent longitudinal lines and away from the end edges.

The absorbent structure with improved handle and feel characteristics may be provided without significant modifications to the equipment that has been utilized to manufacture absorbent structures in the past. For example, to obtain a batt having a thickened central region, one may simultaneously grind one or more and will herein be described in detail a preferred embodiment of the invention and modifications thereof, with the understanding that the present disclosure is to be considered as an exemplification of the principles of the invention and is not intended to limit the invention to the embodiments illustrated. The scope of the invention will be pointed out in the appended claims.

Referring now to the embodiment of FIGS. 1 and 2, a composite absorbent structure is illustrated at 20, and the structure includes a loosely compacted cellulosic fibrous batt 21, and integral therewith, a continuous paper-like, densified, cellulosic fibrous layer 22. The densified layer 22 merges with the loosely compacted batt 21 at a generally planar interface 25, as can be best seen in FIG. 2, and the densified layer includes a plurality of spaced, parallel thickened portions 23 that project beyond the interface 25 and into the batt 21. The thickened portions 23 are produced by an embossing roll, as is hereinafter explained, that provides recesses 24 in the outer surface of the structure in alignment with thickened portions 23. The densified layer 22 extends continuously over one entire face of the absorbent structure, and the thickened portions 23 extend from end to end thereof, as is evident from FIG. 1.

The batt 21 of absorbent structure 20 is formed of loosely compacted short cellulose fibers, such as wood pulp fibers, or cotton linters, or mixtures thereof, which are primarily held together by interfiber bonds requiring no added adhesive, as is known in the art. Briefly, this batt is a low bulk density coherent web of loosely compacted cellulose fibers preferably comminuted wood pulp fibers in the form of so-called "fluff".

The term "short fibers" as used herein, refers to fibers less than about ¼ inch in length, in contrast to "long fibers" or "textile length fibers" which are longer than about ¼ inch in length, and generally are between about ½ inch and 2½ inches in length. The former are substantially less costly than the latter. The classification of fibers by length may be carried out by the Clark Classification Procedure described in the Test Manual of the Technical Association of Pulp And Paper Industry (TAPPI — T233 SU64).

The paper-like densified layer 22 including thickened portions 23 is formed by a slight moistening of one surface of the batt followed by the application of pressure thereto, as is illustrated in FIG. 9, which schematically illustrates the process by which the absorbent structure of the present invention is produced.

A source of compacted short fibers, such as a pulpboard 26 or the like, is fed to an individualizing means, such as a grinding mill 27, which forms a stream of airborne fibers that is drawn onto a traveling belt 28. The compacted fibrous source 26 normally has a moisture content of 5 to 10 weight percent, but the pulpboard may be slightly moistened before grinding if the moisture content is lower, as from prolonged exposure to a dry atmosphere, to bring the moisture of the pulpboard to the desired level before being individualized. The 5 to 10 percent by weight moisture content enables the fibers produced by the grinding operation to have the capability of developing weak interfiber hydrogen bonds which give some coherence to the body of the batt.

The web of fibers deposited upon belt 28 preferably weighs between about 2 and about 10 oz./yd.$^2$. In an exemplary form of the invention, mill 27 grinds the pulpboard into individual short fibers that are deposited in homogeneous fashion on belt 28. In another preferred embodiment, some of the pulpboard fibers are not completely comminuted, and remain joined to other fibers in small clumps, generally smaller than about ¼ inch across. It has been found that the presence of such small clumps of fibers in the body of batt 21 provides islands of increased capacity for holding liquid. Absorbent structures formed in this latter manner may include, for example, from about 2 to about 10 weight percent of fibers in the form of such clumps. The web of fibers laid on belt 28 then passes beneath a compacting roll 29, and the web emerges from beneath roll 29 with a degree of structural integrity as a result of the weak interfiber hydrogen bonds attributable to the moisture in the starting material. The weak hydrogen bonds in the body of batt 21 provide sufficient strength to maintain the integrity of the batt during ordinary handling.

The dense, compacted, paper-like layer or skin 22 is formed on the batt 21 by moistening a surface of the batt with a fine spray of water, and then subjecting the moistened batt to pressure. With reference to FIG. 9, following compaction by roll 29, the web then passes under a nozzle 31 which deposits a fine spray of moisture on the upper surface of the web, as the web is transferred to a further belt 32. The moistened web then passes between a set of calendering rolls 33 and 34, which exert heavy pressure (from about 5 to about 100 or more pounds per square inch, with the commercially preferred range being from about 10 to about 50 pounds per square inch) on the web to form the densified layer or skin 22 on its upper surface.

The formation of the densified skin on the cellulosic batt 21 is believed to be due to the formation of strong hydrogen bonds between contacting moistened fibers, similar to the bonds between the fibers in paper. By the proper selection of the amount of moisture applied to the surface of the batt and by the proper selection of degree of compression imposed, the properties of the densified skin may be varied as desired. The thickness, density, strength and other characteristics of the densified skin will depend upon the uniformity by which the moisture is applied, the depth to which it penetrates, and the degree to which the fibers are compressed. The amount of moisture applied to the web may vary suitably from about 0.0005 to 0.03 cc. of water per square centimeter of web surface, with lesser amounts of moisture being used for thinner webs, and very thin, papery skins and greater amounts for thicker webs and skins of greater thickness. In a typical embodiment, the web is sprayed with about 0.0015 cc. of water per square centimeter of web surface and subjected to a pressure of about 40 lbs./in.$^2$ to obtain a densified, coherent papery skin on the surface of the web which has been moistened. The strong hydrogen bonds created by the compression of the moistened web markedly increases the cohesive strength of the resulting composite absorbent structure.

Following formation of the continuous densified layer 22, the web passes between an embossing roll 35 and a back up roll 36, with the embossing roll 35 being shown in detail in FIG. 8. Embossing roll 35, which is rotated by conventional power means, not shown, includes a plurality of axially spaced cylindrical portions 37 of equal diameter, and a plurality of annular rib-like projections 38 between cylindrical portions 37. Embossing roll 35 and back up roll 36 may be mounted for vertical adjustment relative to one another, but in any further pulp boards narrower than the wider pulp board and centered with respect thereto.

Depending upon the amount of moisture applied and the degree of compaction, the thickened portions may be coherent and unitary, i.e. any zone within the thickened portion has a density greater than the density of the remainder of the absorbent product above the densified layer; or the thickened portions may include densified fibrous strata which surround pores or voids that are essentially free of fibers and which have a density that is substantially zero, and in any case substantially less than the density of the remainder of the absorbent product above the continuous densified layer. This latter type of densified structure provides an increased volumetric storage capacity and an increased volumetric carrying capacity as compared to cohesive or unitary thickened portions containing the same total amount of fibers.

The apparatus for producing the selectively thickened densified layer of the batt portion may include spaced calendar rolls for applying pressure to a fibrous web after it has been moistened to form a continuous densified layer on one side of the web, and a ribbed embossing roll which cooperates with a back-up roll to form the thickened portions of the densified layer. In an absorbent structure wherein the thickened densified portions of the batt extend completely through the cross-sectional thickness of the batt, the ribs on the embossing roll are spaced in close proximity to the periphery of the back-up roll, and when the entire central region of the batt is thickened, the ribs in the center of the embossing roll may have a smaller outer diameter than the ribs at the outer portions of the roll. When the continuous densified layer is formed on the batt having the thickened central region, it is preferred to use cylindrical calendar rolls, since this results in the application of greater pressure to the central region of the batt to form a densified layer which is thickened throughout this area (in addition to the localized thickening derived from the embossing roll). The absorbent structure which includes a batt having a continuous densified layer that is thickened throughout its center functions in an improved manner, as compared to a batt having a continuous densified layer of equal thickness, since the absorbent structure is usually wetted in the central area, and the increased thickness of the densified layer provides a vehicle for more rapidly transporting a larger volume of fluid from the initially wetted area. The further thickened densified lines in the thickened central region of the continuous densified layer provide a further means for directing fluid to remote areas of the densified layer. The thickened central portion of the continuous densified layer also increases the volumetric storage capacity of the densified layer, so that a larger volume of fluid may be retained in spaced relationship with respect to the surface of the absorbent structure opposite the densified layer.

BRIEF DESCRIPTION OF THE DRAWINGS

FIG. 1 is a plan view of a first embodiment of the absorbent structure of the present invention showing in broken lines the pattern of spread in the densified layer of a given quantity of fluid;

FIG. 2 is an enlarged cross-sectional view taken generally along line 2—2 of FIG. 1;

FIG. 9 is a schematic side elevational view illustrating a process by which an absorbent structure of the present invention may be produced;

FIGS. 10 and 12 are plan views of prior art absorbent structures, with FIG. 10 including a plurality of spaced, parallel longitudinally extending paper-like densified portions, and with FIG. 12 including a continuous paper-like densified portion throughout the entire area of one side thereof, with each view showing in broken lines the pattern of spread in the densified layer of a given quantity of fluid;

FIGS. 11 and 13 are enlarged cross-sectional views taken generally along lines 11—11 and 13—13 of FIGS. 10 and 12, respectively;

FIG. 22 is a graph illustrating the relationship between compression force and water add-on in connection with the embodiment illustrated in FIGS. 20 and 21;

FIGS. 23–26 are graphs showing the relationship between compression force and density at various moisture add-on levels in connection with the embodiment illustrated in FIGS. 20 and 21.

DESCRIPTION OF THE PREFERRED EMBODIMENTS

Figure 3:
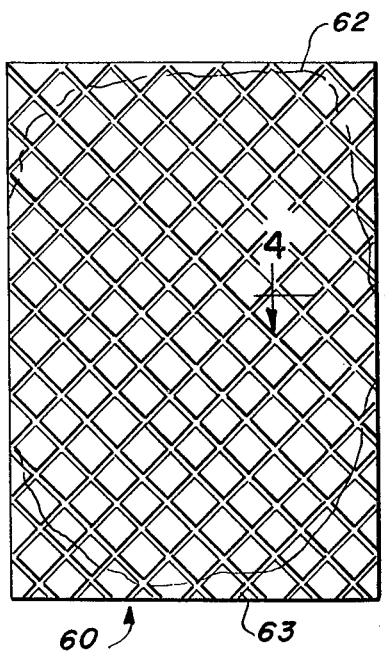
FIG. 3 is a plan view of a second embodiment of the absorbent structure of the present invention showing in broken lines the pattern of spread in the densified layer of a given quantity of fluid.

While this invention is susceptible of embodiment in many different forms, there is shown in the drawings event, the spacing between the rolls is selected so that the projections 38 engage and compress the previously formed densified layer 22.

The amount of moisture that is applied to the web by nozzle 31 is adequate to retain the fibers beneath the densified skin 22 moistened after the web passes beneath calendering rolls 33, 34. Thus, when the web is subjected to further compression by embossing roll 35, the projections 38 form the thickened densified portions 23 and the ribs 24 in the outer surface of the densified layer. As in clear from FIG. 2, the projections 38 cause the thickened portions 23 to extend into the loosely compacted batt portion 21 through the interface 25 between the batt portion 21 and the densified layer 22. The thickened densified portions 23, by virtue of their penetration into the loosely compacted batt portion 21, provide a three dimensional shear resisting strengthening effect that significantly increases the strength and cohesiveness of the composite absorbent structure.

Following formation of the thickened densified portions 23 and ribs 24, the web may be transported by a take away conveyor 39 to a winding station where the web is taken up by a storage roll (not shown), or alternatively, the web may pass through a cutting station where a severing mechanism cuts the web into individual absorbent structures, as illustrated in FIG. 1.

The short fibers used in making the composite absorbent structures 20 of this invention are generally entirely fibers of wood pulp or cotton linters. However, other cellulosic fibers may be used, as well as blends of cellulose fibers with other fibers such as silk, wool, nylon and cellulose acetate. Highly purified kraft paper pulp fibers have proven to be most satisfactory for most applications.

Absorbent structures as described above may be used in a wide variety of end products, such as disposable diapers, sanitary napkins, bed pads, surgial dressings, and similar products intended to absorb body fluids. The thickened portions 23 of the densified layer, in addition to adding strength to the composite structure, provide a means for transporting an increased volume of liquid in the direction of the thickened portions. This attribute, together with the increased volumetric storage capacity due to the increased cross-sectional area in the densified layer, as compared to a densified layer of uniform thickness, make the absorbent structure extremely well suited for use in end products adapted to absorb body fluids. The improved flow characteristics attributable to the thickened densified portions 23 will be best understood by comparing the flow pattern shown in broken lines in FIG. 1 to the flow patterns shown in broken lines in the prior art structures illustrated in FIGS. 10 and 12, and before discussing the flow patterns in detail, the prior art structures will be described.

FIGS. 10 and 11 illustrate a composite absorbent structure 40 which includes a highly porous, loosely compacted cellulosic fibrous batt 41, and integral therewith, a plurality of spaced, parallel, paper-like, densified cellulosic fibrous strips 42. As is evident from FIG. 11, the densified strips, or rows 42, are separated by loosely compacted batt portions 41. FIGS. 12 and 13 illustrate a composite absorbent structure 50, which includes a highly porous loosely compacted cellulosic fibrous batt 51, and integral therewith, a continuous paper-like, densified, cellulosic fibrous layer 52 of uniform thickness.

For purposes of comparison, in order to evaluate the spread of fluid in the denisified layer of the absorbent structure of the present invention illustrated in FIGS. 1 and 2, and to relate the spread to the spread of the prior art structures illustrated in FIGS. 10–13, a source of short fibers in the form of bleached Kraft pulp was ground with a Fitzmill and the resulting web was subjected to calendering pressure, as by roll 29. The samples were formed by cutting the web into 11 inches by 15 inches panels which weighed in the range of from 21 to 23 grams, and an identical amount of water (2.7 grams per panel) was sprayed on to each panel.

A first panel was subjected to line embossing to form spaced parallel densified strips, such as shown at 42 in FIGS. 10 and 11. A second panel was subjected to uniform pressure throughout its width following the spraying of water, and a continuous paper-like, densified skin, such as shown at 52 in FIGS. 12 and 13 was formed on the panel. A third panel was subjected to the same calendering pressure as the second panel to form a densified layer such as shown at 22 in FIGS. 1 and 2, and following calendering, the panel was subjected to line embossing to form thickened densified portions, such as shown at 23 in FIGS. 1 and 2.

After the panels were formed as described above, each was placed on a plane backed up with a polyethylene film and covered with a sheet of stabilized pulp. Thirty cc. of stained liquid was introduced to the midportion of each panel by means of buret, and in each instance, because of the increased capillary pressure provided by the densified portions, the liquid was drawn through the stabilized pulp, and through the loosely compacted batt portions of the composite absorbent panels into the densified portions.

Referring first to FIG. 12, because the skin 52 is of uniform density and coextensive with one face of the composite structure 50, once the skin 52 is wetted, it tends to spread the liquid outwardly in all directions at an equal rate. Thus, in products that are rectangular, such as shown by the broken line spread pattern in FIG. 12, the fluid will reach the side edges of the absorbent structure before it utilizes the entire absorbent capacity of the densified layer, with the result that the fluid tends to leak around the side edges of the structure.

With reference to FIG. 10, the fluid tends to flow rapidly along the spaced, parallel densified zones 42, and to spread outwardly across the loosely compacted batt portions 41 at a much slower rate. As is evident from the broken line spread pattern illustrated in FIG. 10, the liquid has spread outwardly beyond the outermost densified zones 42 by only a slight amount, but has reached the ends of the densified portions, with the result of fluid leakage at the ends of the absorbent structure.

In the embodiment of FIGS. 1 and 2, the liquid is transported relatively rapidly in all direction of the densified layer of the absorbent structure, because the densified layer is continuous over one face thereof. However, the thickened portions 23 provide for an increased volumetric flow rate in the longitudinal direction to rapidly move a larger volume as compared to the embodiment of FIGS. 12 and 13, toward the ends of the absorbent structure. The bridging portions provided by the portions of densified layer between the thickened portions rapidly transport the liquid away from the initially wetted area, and into contact with previously unwetted thickened portions, with the result that liquid is rapidly drawn away from the initially wetted area and transported both longitudinally and transversely into substantially all portions of the densified layer. As is evident from the spread patterns shown in broken lines in FIG. 1, the liquid has spread laterally outwardly a greater amount than in the discontinuous densified layer embodiment of FIGS. 10 and 11, and no fluid has reached the side or longitudinal edges of the product.

Figure 4:
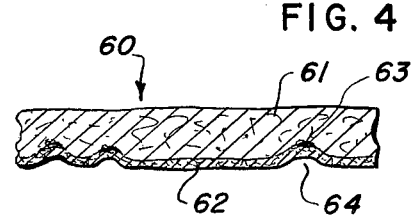
FIG. 4 is an enlarged cross-sectional view taken generally along line 4—4 of FIG. 3.

Referring now to FIGS. 3 and 4, a second embodiment of the composite absorbent structure of the present invention is illustrated generally at 60, and absorbent structure 60 is similar to previously described absorbent structure 20 in that is includes a highly porous, loosely compacted cellulosic fibrous batt 61 having integral therewith, a continuous paper-like, densified, cellulosic fibrous layer 62 having selectively thickened portions 63. However, as distinct from the embodiment of FIGS. 1 and 2, in the embodiment of FIGS. 3 and 4, the thickened densified portions 63 are provided by first and second groups of spaced parallel lines or rows, with the rows being disposed at an angle to one another and at an angle with respect to the length of the product. As is evident from FIG. 3, in the illustrated embodiment, the thickened densified rows of each group are disposed at right angles to one another to provide a diamond-like gridwork of unthickened densified portions 62.

Figure 7:
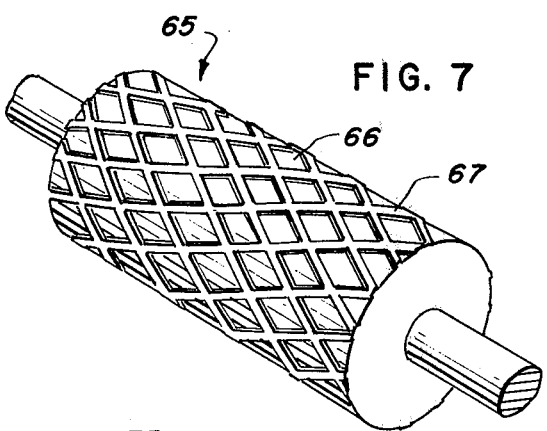
FIG. 7 is a perspective view of an embossing roll used to produce the pattern illustrated in FIGS. 3 and 5.
Figure 8:
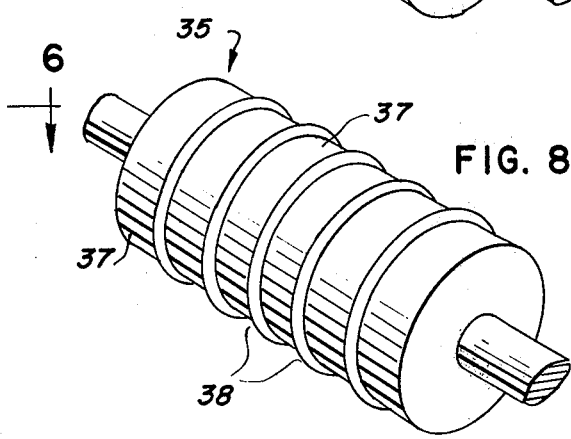
FIG. 8 is an enlarged perspective view of an embossing roll used to produce the configuration illustrated in FIG. 1.

The configuration of FIGS. 3 and 4 may be produced by substituting an embossing roll 65 (FIG. 7) for the embossing roll 35 of FIG. 9, and embossing roll 65 includes a plurality of spaced parallel rows of inclined projections 67 that surround diamond-like recesses 66. It will be appreciated that when the absorbent structure 60 is subjected to compression by the embossing roll 65, the projections 67 form the thickened densified portions 63, and the recesses 64 in alignment therewith. As with the embodiment of FIGS. 1 and 2, the thickened densified portions 63 provide an increase in strength for the composite absorbent structure by virtue of their extension into the loosely compacted absorbent batt 61. The thickened densified portions 63 also provide a greater cross-sectional area which has an increased volumetric storage capacity.

In the embodiment of FIGS. 3 and 4, by virtue of having the groups of densified lines disposed at an angle with respect to one another, a multiplicity of intersections is created, so that liquid spreading outwardly in the densified layer away from an initially wetted area will rapidly encounter additional thickened densified portions with the net result that the fluid will be transported outwardly at a rapid rate to utilize substantially the entire absorptive capacity of the densified layer. As is clear from the broken line fluid spread pattern shown in FIG. 3, the inclined thickened densified portions transport fluid to the remote corners of the absorbent structure, as well as the side and longitudinal edges thereof without any leakage occurring around the perimeter of the absorbent structure.

Figure 6:
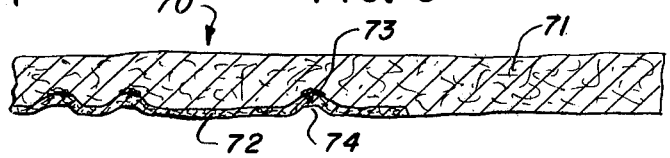
FIG. 6 is an enlarged cross-sectional view taken generally along line 6—6 of FIG. 5.
Figure 5:
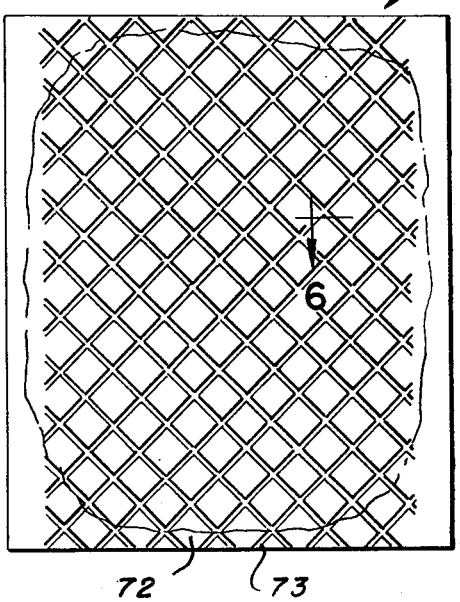
FIG. 5 is a plan view similar to FIG. 3, but illustrating a modification thereof.

Referring now to the embodiments of FIGS. 5 and 6, an absorbent structure 70 is illustrated therein that is similar to the embodiment of FIGS. 3 and 4, in that the densified layer 72 integral with the loosely compacted batt 71 includes thickened portions 73 defined by oppositely inclined groups of spaced parallel thickened lines. However, as distinct from the embodiment of FIGS. 3 and 4, the densified skin 72 does not extend to the lateral edges of the absorbent structure 70, although the skin does extend over a major area of the surface of the batt as shown in FIG. 6 and instead, the loosely compacted batt 71 is provided outwardly of the side edges of the densified layer. The lesser wickability attributable to the presence of the loosely compacted batt at the lateral edges of the structure provides a barrier that resists any tendency of fluid leakage at the side edges of the absorbent structure. The method of forming this embodiment will be discussed in detail below.

Figure 15:
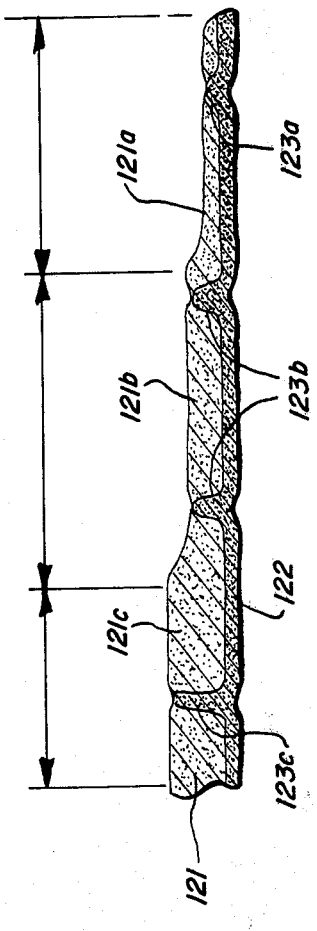
FIG. 15 is an enlarged partial cross section, illustrating a further modification including a stepped contoured batt portion.

In certain instances, as in an absorbent structure designed for use in a sanitary napkin intended for periods of heavy discharge or in a disposable diaper or bed pad where weight is likely to be applied in its central region, the batt may have an increased thickness in the center thereof. Referring to FIG. 15 the absorbent structure illustrated therein is similar to the embodiment of FIGS. 1 and 2 so that similar reference numerals, increased by 100, have been used to designate those elements in FIGS. 1 and 2 which correspond with those in FIG. 15. In the past, when it was desired to provide a sanitary napkin with an increased volumetric storage capacity, a separate or folded layer of batt material was provided to increase the capacity of the absorbent structure. These structures functioned satisfactorily for their intended purpose, and the absorbent structure of the present invention represents an improvement thereon by eliminating the need for a separate element or a fold-over double thickness, while at the same time providing a more gradual transition between the unthickened and thickened portions of the batt.

It will be noted in FIG. 15 that the batt 121 has a stepped cross-sectional configuration including thin, light-weight marginal sections 121a, somewhat thicker, somewhat heavier intermediate sections 121b, and a thickest, heaviest central section 121c. As is evident from FIG. 15, there is a smooth transition between batt sections 121a and 121b and between batt sections 121b and 121c, and the gradually stepped unitary construction of the absorbent structure improves the handle and feel thereof, particularly as compared to a structure that is thickened in its central region by use of a separate batt layer. The weight (i.e., pounds/inches$^2$) of the central sections 121c is preferably about twice that of the side sections 121a while the weight of the intermediate sections 121b is preferably about one-half times that of the side sections 121a. The contoured batt 121 is compressed during calendering to form the selectively thickened densified layer 122 (hereinafter described) so that the density of at least central section 121c is increased relative to the density of side sections 121a.

Figure 14:
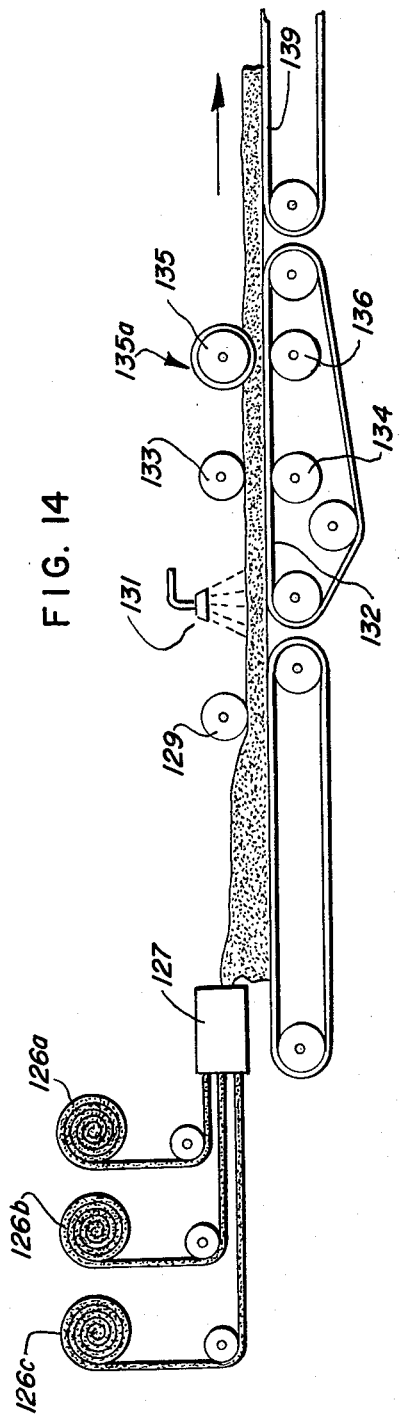
FIG. 14 is a schematic side elevational view illustrating a process by which an absorbent structure of the present invention may be produced.

The absorbent structure illustrated in FIG. 15 may be provided by simultaneously feeding three rolls of compacted wood pulp material to a grinding mill. As shown in FIG. 14, roll 126a provides a first source of fibers, with roll 126b, which is narrower than roll 126a and centrally disposed relative thereto, providing a second source of fibers, and with roll 126c which is narrower than roll 126b and centrally disposed relative thereto, provides a third source of fibers. The compacted wood pulp materials from rolls 126a–126c may be simultaneously ground in mill 127 and deposited upon belt 128 to thereby produce the contoured and centrally thickened batt 121 as shown in FIG. 15.

The selectively thickened densified layer 122 is formed as described above by moistening the deposited web, and subjecting the web to calendering and embossing pressure. With reference to FIG. 14, the web from belt 128 initially passes under compaction roll 129, and a preselected quantity of moisture is applied to the surface of the web, as by nozzle 131. The web then passes between the nip of calendering rolls 133 and 134, and the present invention contemplates that the rolls 133 and 134 will be cylindrical in shape even though the web has a stepped or contoured configuration. It has been found that by subjecting such a web to calendering pressure applied by cylindrical rolls, the densified layer 122 is thicker in the central region of the web than it is in the side margins thereof. By virtue of this construction, a larger volume of liquid can be retained in the central region of the absorbent structure as compared to a construction which includes a densified portion of uniform thickness.

The present invention also contemplates that the densified portion 122 which is thicker in its central region will also include a plurality of spaced, selectively further thickened portions, as in the previously described embodiments. To this end, while the surface of the batt is still moist, it is subjected to embossing pressure between an embossing roll 135 and a backup roll 136, with the embossing roll 135 having spaced ribs 135a thereon that produce longitudinally extending selectively thickened lines designated 123a, 123b, and 123c in FIG. 14. These spaced, selectively thickened densified portions preferably extend through a substantial portion of the cross-sectional thickness of batt 121, and most preferably, these portions extend entirely through the cross-sectional thickness of the batt so as to be visible upon the surface of the batt opposite that including the continuous densified layer 122. It should be noted that this latter feature is desirable in batts of uniform cross-sectional thickness, as in batts having a stepped construction as illustrated in FIG. 15. It should also be noted that in a batt having a stepped construction, the thicker densified portions 123a are shorter than the thicker densified portions 123b, which in turn are shorter than the thickened densified portions 123c.

The upper portions, i.e., the portions opposite densified layer 122, of such densified lines 123a, 123b, and 123c are spaced downwardly slightly from the upper surface of the batt. This spacing enhances the cushioning effect and overall feel of the absorbent structure. The downward spacings are provided by virtue of the fact that embossing roll 135 is positioned beneath the batt, as compared to embossing roll 35, which is positioned above that batt, as is clear from FIGS. 9 and 14. Embossing roll 135 is positioned closely adjacent to backup roll 136 to define a confined nip, whereat sufficient pressure is applied to the fibers on the unmoistened side of the batt to cause the moisture to wick through the entire cross-sectional thickness of the batt. Because of the pressure concentration between the smooth uncompressible surfaces of the ribs on the embossing roll and the facing surface of the backup roll, the upper ends of the thickened lines are given a density that is substantially the same as the density of the outer face of layer 122. Since the fibers in the midportion of the thickened lines are compressed against one another, the density in the middle of the thickened lines is less than the density of the ends of the lines, or of the continuous skin 122, although the density of the middle of the lines is significantly greater than the density of the loosely compacted fluff portions adjacent the lines. The ribs 135a in the center of embossing roll 135 may have a reduced outer diameter, as compared to the ribs at the outer ends of the embossing roll, so that substantially uniform embossing pressure will be applied to the various portions of the batt.

In a batt construction which includes a continuous densified portion at one side thereof, with a plurality of spaced, selectively thickened further densified portions that extend completely through the cross-sectional thickness of the batt, a construction is produced which has significantly improved strength characteristics as compared to a batt having densified layers of uniform thickness, or even to a batt having a continuous densified layer that includes selectively thickened areas. The three dimensional strengthening effect attributable to the selectively thickened densified portion of increased height enables the remaining loosely compacted fluff portion of the batt to have a lower density than heretofore thought possible. In this regard, in the past in the production of batts of the type described herein the wood pulp starting material was premoistened prior to grinding, so that after the fibers weree deposited in the form of a web and subjected to compaction, weak hydrogen bonds were formed in the loosely compacted batt portion to give the batt some degree of structural integrity. In producing batts wherein the selectively thickened densified portions extend either all the way through the cross-sectional thickness of the batt, or through a major portion of the cross-sectional thickness thereof, the step of premoistening the starting material is preferably eliminated entirely, so that the loosely compacted portion of the batt will be extremely light and fluffy. The overall density of the batt layer will be within the above mentioned range due to the presence of additional densified material within the densified lines of increased height, but the presence of the less dense loosely compacted portions makes the batt layer more conformable. This improved property is obtained without sacrificing any volumetric storage capacity, since the batt layer can include approximately the same number of fibers as previously known comparable batts.

The thickened densified lines 123a-123c, in addition to strengthening the batt, also provide a mechanism for transporting a larger volume of fluid from an initially wetted area to remote areas of the densified layer 122, and in addition provide an increased storage capacity within the densified layer itself. As with the previously described embodiments, the portions of the densified layer 122 between the thickened lines 123a-123c function as bridging portions, so that liquid migrating outwardly from an initially wetted area encounters additional thickened lines which cause the liquid to rapidly spread longitudinally of the batt.

Figure 16:
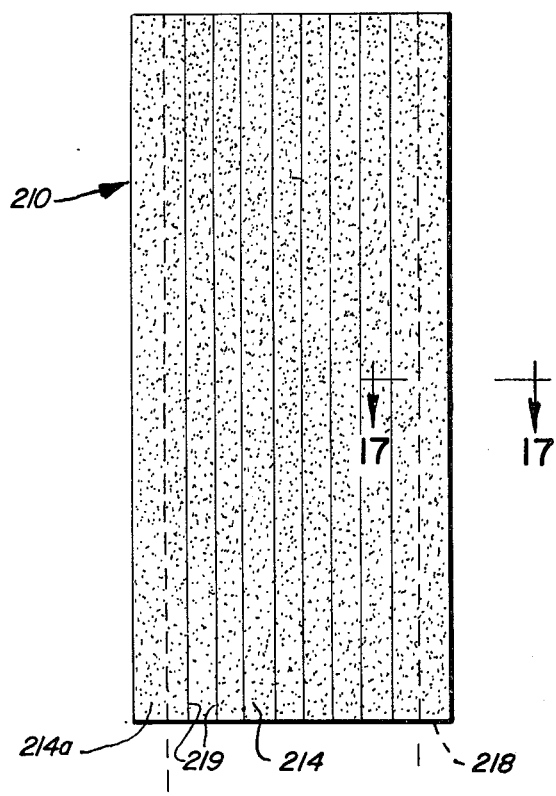
FIG. 16 is a plan view, similar to FIG. 1, illustrating a further modification thereof.
Figure 17:
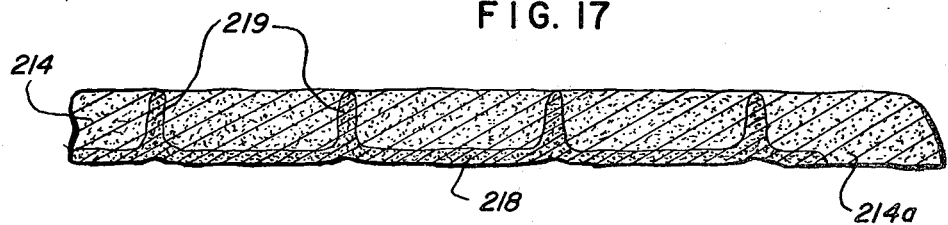
FIG. 17 is an enlarged partial cross section of the absorbent structure of FIG. 16 taken along plane 17—17.

Referring now to FIGS. 16 and 17, a further absorbent structure 210 is illustrated therein which is similar to the previous embodiments in that is shows an absorbent panel or batt 214, as set forth above, formed of loosely compacted short cellulose fibers, such as wood pulp fibers, or cotton linters, or mixtures thereof; and including a continuous paper-like densified highly compacted lowermost fibrous layer or skin 218 that includes spaced parallel, thickened densified portions 219 which extend completely through the cross-sectional thickness of the batt, as in the embodiment of FIG. 15. However, unlike the previously described embodiment of FIG. 15, densified layer 218 does not completely cover the side of the batt. Instead, the continuous densified layer 218 is limited to the central area of the batt as in FIGS. 5 and 6, so that loosely compacted portions 214a are provided outwardly of the side marginal edges thereof. The loosely compacted strips 214a, which are of equal width and which extend from end to end of the batt 214 in the embodiment of FIGS. 16 and 17 serve to slow up the spread of liquid, and minimize the possibility of liquid wicking beyond the sides of the batt.

Figure 16A:
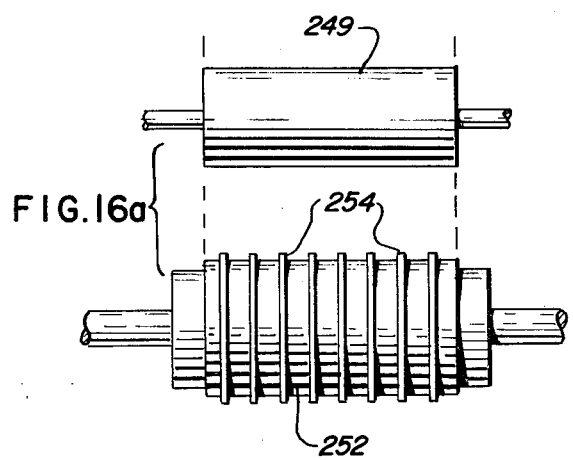
FIG. 16a is a side elevational view of the rolls that are used in the manufacture of the embodiment of FIG. 16.

Densified layer 218 is formed in the manner described above, i.e., by moistening one side of the deposited layer of fibers and then serially subjecting the layer to calendering pressure to form the continuous densified layer and then to embossing pressure to form the thickness densified portions 219. With reference to FIG. 16a, a calendering roll 249 is shown therein which has a cylindrical configuration, and which has a length that is less than the width of batt 214. When the premoistened batt passes between roll 249 and a backup roll (not shown), the centralized continuous densified portion 218 is formed, and since no calendering pressure is applied to the side portions 214a of the batt, these portions remain loosely compacted. The batt layer, while still moist, then passes between an embossing roll 252 and a backup roll (not shown); and spaced, circumferentially continuous ribs 254 on roll 252 form the thickened densified ribs or lines 219.

With the above-described arrangement, where the calendering roll 249 and embossing roll 252 are narrower than the width of the batt 214, it is not critical to control the application of moisture to the batt and the entire surface of the batt can be moistened without having the densified portion 218 extend completely to the side marginal edges of the batt. However, if desired, moisture may be applied to only the central portion of the batt, in which case it is not critical to control the width of the calendering and embossing rolls.

Figure 18:
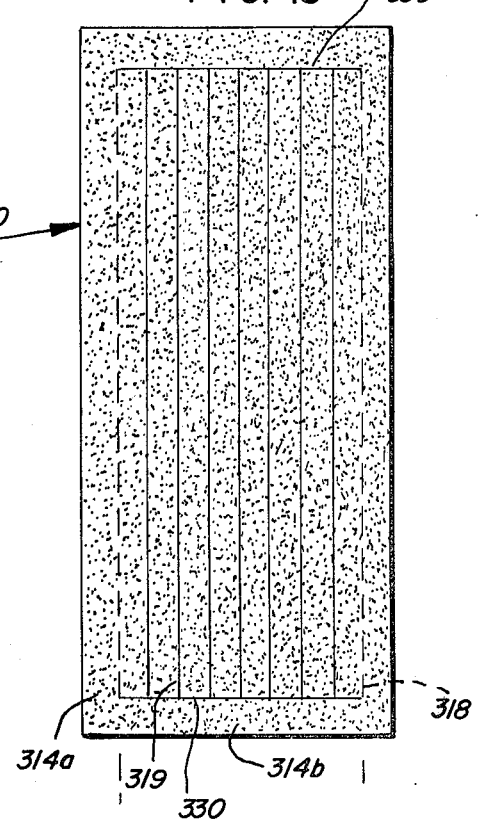
FIG. 18 is a top elevation view, similar to FIG. 16, and illustrating a still further embodiment of the invention.

Referring now to FIG. 18, a still further absorbent structure 310 is shown therein which is similar to the embodiment of FIGS. 16 and 17, so that similar reference numerals (increased by 100) have been used to designate the elements in FIG. 18 which correspond with those in FIGS. 17 and 18. The absorbent structure 310 differs from the absorbent structure 210 in that, in addition to having loosely compacted portions 314a outwardly of the sides of a central densified portion 318 on one side of the batt, batt 314 also has loosely compacted portions 314b outwardly of the ends of densified portion 318. This arrangement may be provided by subjecting the premoistened batt to embossing pressure between a backup roll (not shown) and an embossing roll 349 that is narrower than the batt and disposed centrally relative thereto, and which includes an axially extending portion 349b having a reduced diameter as compared to the remainder of the roll. Subsequent to calendering, the still moist batt layer passes between an embossing roll 352 and a backup roll (not shown) to form the thickened densified portions 319. As is clear from FIG. 19, ribs 354 are circumferentially discontinuous to provide a reduced diameter portion 354b which corresponds with reduced diameter portion 349b. It will be understood that when the structure 310 is formed on an assembly line, such as that shown schematically in FIG. 14, the device (not shown) that severs the batt layer into individual batts is synchronized with calendering roll 349 and embossing roll 352 to cut the uncompacted batt portions left by reduced diameter roll portions 349b and 354b substantially medially thereof, so that the loosely compacted portions 314b at opposite ends of the batt are of substantially equal size.

It will be understood that with the arrangement described immediately above, loosely compacted batt portions 314a and 314b cooperate to provide substantially less dense zones that completely surround densified layer 318 and which effectively limit the likelihood of liquid wicking to the edges of the densified layer of the batt and leaking from the edges. In addition to being formed as described above, the present invention also contemplates that the limited densified layer 319 may be formed by moistening only the central area of the batt, and then applying calendering and embossing pressure thereto. It should also be noted that rolls 349 and 352 could be coextensive in length with the width of the batt, so that the densified layer would extend completely across the width of the batt, with loosely compacted portions 314b being present outwardly of each end of the densified layer.

All of the above-described embodiments in which the thickened densified lines extend continuously through the length of the absorbent structure may be further modified by providing transverse densified lines near the end edges of the structure. The transverse densified lines provide a mechanism for transferring fluid flow from the longitudinally extending thickened lines or strips to adjacent thickened lines so that fluid flowing towards the end edges of the structure will be transferred to adjacent thickened densified lines or strips and thereby minimize the possibility of fluid leakage of the end edges of the absorbent structure.

Figure 19:
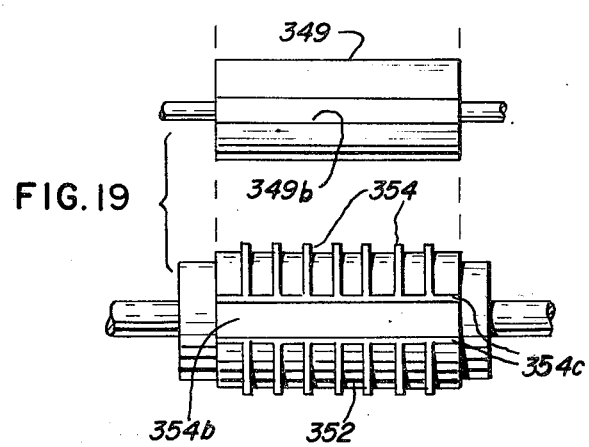
FIG. 19 is a side elevational view of rolls that are used in the manufacture of the embodiment of FIG. 18.

Referring to FIGS. 18 and 19, the transverse densified lines 330 are formed at or near the end edges of the densified layer 318. This arrangement may be provided by subjecting the premoistened batt to transverse embossing pressure during the formation of the longitudinal densified lines 319. The embossing pressure is provided by axial ribs 354c which are located adjacent the reduced diameter portion 354b on embossing roll 352. The two axial ribs 354c extend completely across the width of the embossing roll surface so that the transverse densified lines 330 extend across the entire end edges of the thickened densified layer 318 to rapidly transfer fluid flow in the densified layer 318 to adjacent portions of the densified layer and adjacent longitudinal transverse lines 319.

The transverse densified lines 330 may be used in combination with the unthickened end edge portions 314b to further increase the protective barrier means against liquid leakage out the end edges of the absorbent structure. It will also be appreciated that the transverse densified lines will function to transfer fluid flow laterally in absorbent structures of the present invention which do not include loosely compacted end portions similar to 314b. The transverse thickened lines 330 may also be provided by a plurality of thickened lines in close spaced relationship to the ends of the absorbent structure to further increase the rate of fluid transfer at the end edges of the absorbent structure.

While the thickened densified lines 23, 123, 219 and 319 in each of the previously described embodiments have been illustrated as being continuous in length, it should be understood that the present invention is not limited thereto, since the thickened lines may also be discontinuous and formed, for example, by a plurality of relatively closely spaced thickened strips or sections. While it is not desired to be limited to any specific dimensions, the thickened densified strips may be about 1½ inches long and separated from one another by about ¼ inch. Most preferably, the thickened densified strips of adjacent lines are staggered relative to one another, so that the unthickened densified portions between the thickened strips are adjacent the midportions of the thickened strips of adjacent lines. Such discontinuous or intermittent thickened densified lines may be formed by subjecting a still moistened web having a continuous densified layer over a given area of one face thereof to embossing pressure applied by an embossing roll having a plurality of axially spaced ribs each defined by a plurality of circumferentially spaced rib segments that are adapted to form spaced thickened densified strips.

Absorbent structures having a continuous densified layer over a given area of one face thereof, with thickened intermittent or discontinuous lines formed therein, have been found to have improved feel and conformability, as compared to similar absorbent structures having continuous thickened densified lines. The unthickened portions between the thickened strips provide less stiff zones, or in effect hinges, at a multiplicity of spaced locations within the structure to enable the structure to be placed in close fitting conformity during use. Since the thickened densified strips are spaced relatively closely to one another, the strips of each line collectively cooperate to rapidly spread liquid outwardly in the directions of the lines, so that the improved conformability characteristic is provided with little or no loss in fluid directing properties. All of the thickened densified lines need not be discontinuous to provide the improved feel and conformability characteristics, and the present invention also contemplates that a combination of continuous and discontinuous thickened lines may be provided. Furthermore, the thickened densified strips of the discontinuous thickened lines, and the spacing between the thickened strips, need not be the same within each line, or in adjacent lines. It is desired that the thickened densified strips of the densified lines comprise from about 75% to about 95% of the total length of the lines.

Figure 27:
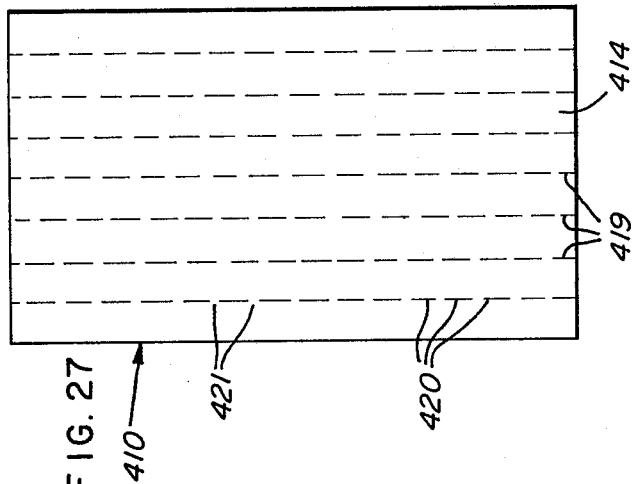
FIG. 27 is a plan view, similar to FIG. 1, illustrating a further modification of the absorbent structure of this invention.

FIG. 27 illustrates just described embodiment and shows absorbent structure 410 comprising absorbent panel or batt 414, formed of loosely compacted cellulose fibers; and including a continuous paper-like densified highly compacted fibrous layer or skin (not shown in FIG. 27) which includes spaced parallel, thickened lines 419 which extend through the thickness of the batt. Each line is discontinuous and consists of thickened portions 420 and unthickened spaces 421, the spaces being arranged in staggered relationship so that the spaces in adjacent lines are not side-by-side.

Although all of the absorbent products described above have the continuous densified layer on an external surface thereof, the invention is not limited thereto, in that it is comtemplated that the continuous densified layer may be provided interiorly of the absorbent product.

The terms "thickened lines" or "thickened portions", as uded herein, are intended to refer to limited areas (as compared to the total area of the fibrous structure) in which at least some of the fibers above the continuous densified skin are more closely compacted than the fibers above the continuous densified skin in other areas of the fibrous structure, and the terms "thickened lines" or "thickened portions" are meant to apply to both the coherent or unitary structures of FIGS. 1–19 and to structures having voids, pores, or gaps therein as shown in FIGS. 20–26. Within the areas designated as "thickened lines" or "thickened portions", the densities (whether calculated on the basis of total volumes within these areas or on the basis of the volumes of the compacted portions without the voids) are higher than the density in other portions of the fibrous structure above the continuous densified skin. The "thickened lines" or "thickened portions" as defined above can extend completely or partially through the cross-sectional thickness of the fibrous structure, it being understood that the amount of thickening is dependent upon the extent to which it is desired to rapidly transport fluid away from an initially wetted area and the degree to which it is desired to reinforce the fibrous structure.

Figure 20:
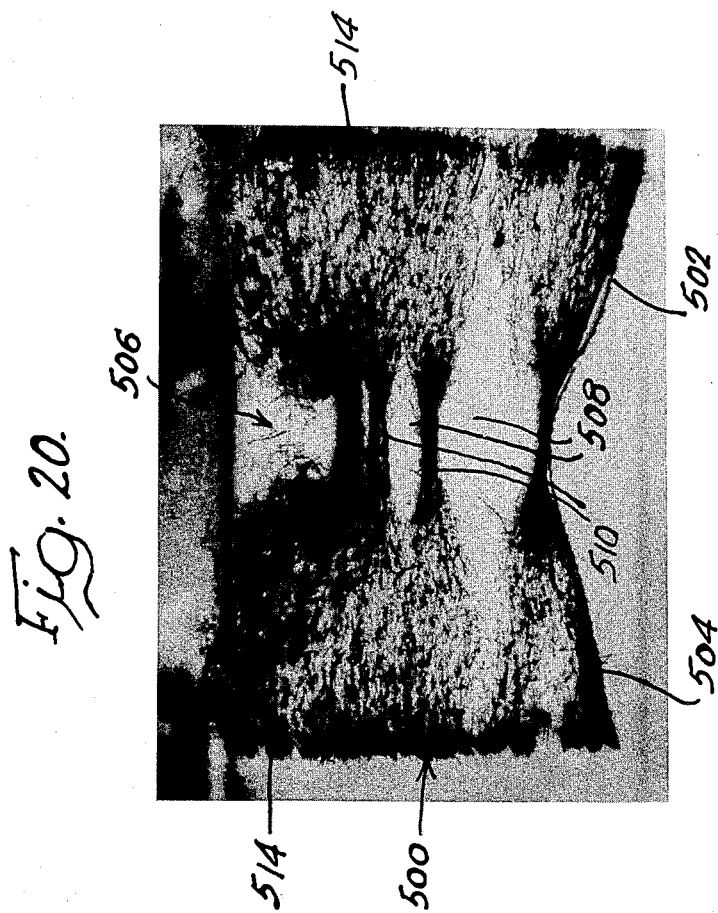
FIG. 20 is a photomicrograph of a cross section of yet another embodiment of the absorbent structure of the present invention taken transversely to the length of the thickened line.
Figure 21:
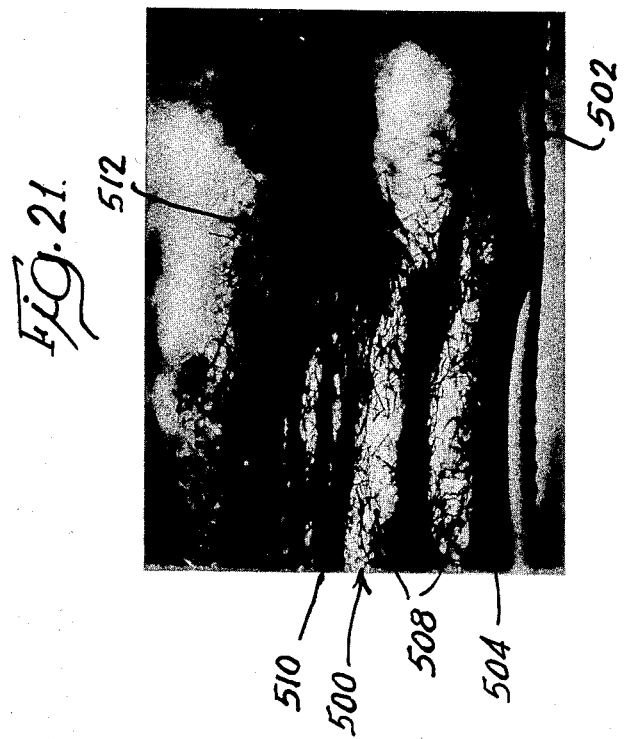
FIG. 21 is a photomicrograph of an absorbent product as illustrated in FIG. 20 and taken in the direction of the thickened line.
Figure 25:
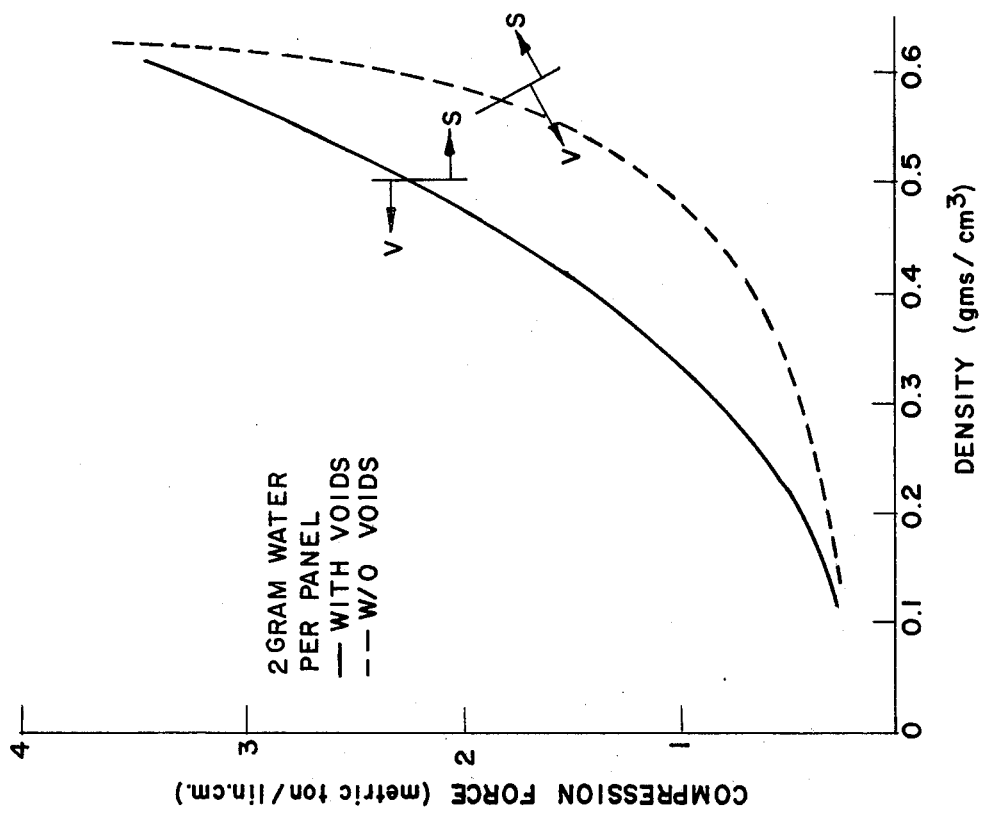
Figure 24:
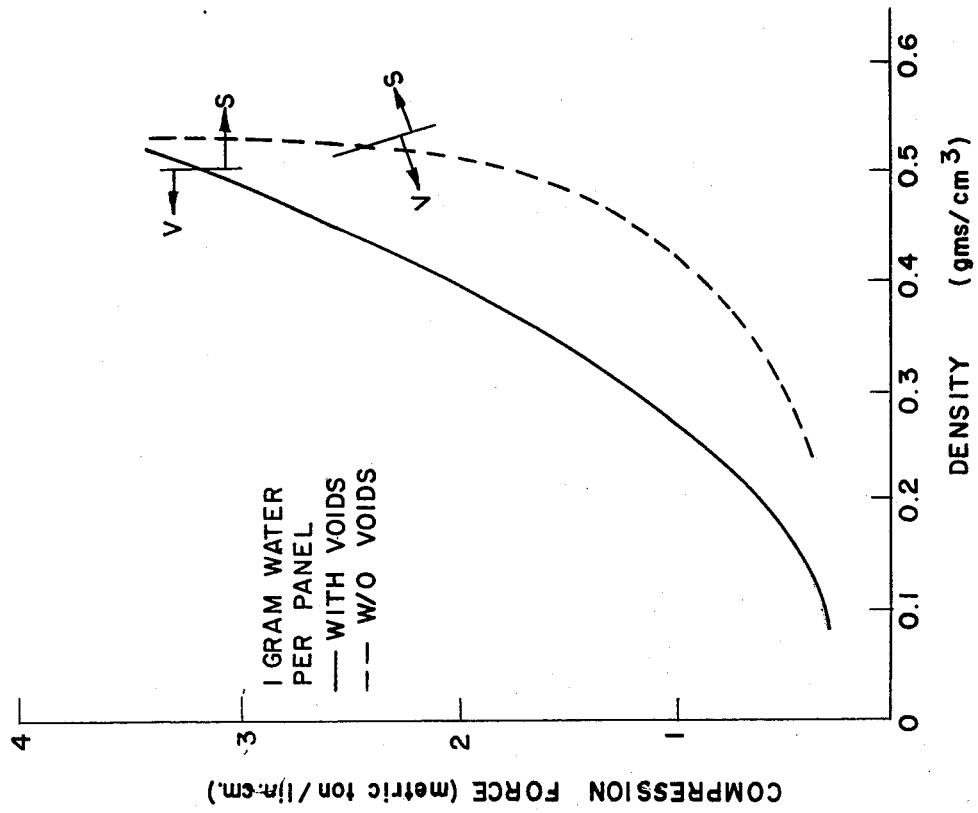
Figure 26:
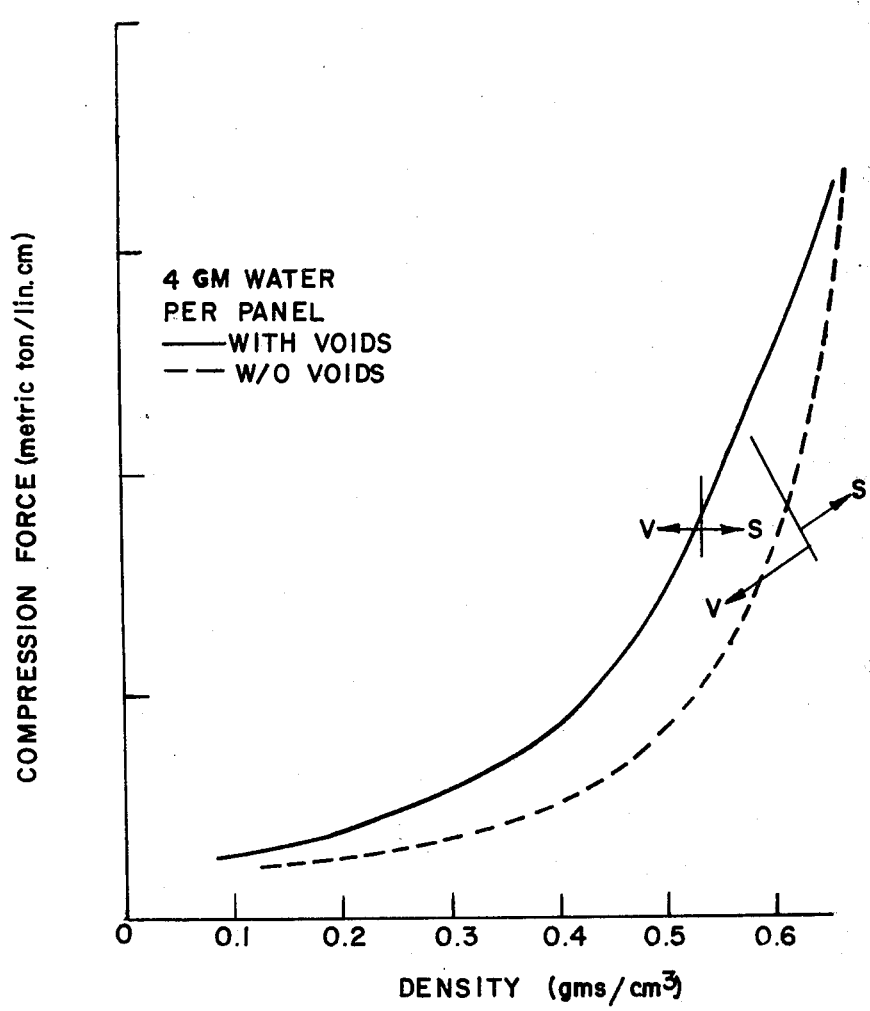

With specific reference to FIGS. 20 and 21, the absorbent product is designated in its entirety by reference numeral 500, and is shown attached to a backing sheet 502, which may be formed of a polyethelene film or other suitable film depending on the end use of the absorbent product. As with the previous embodiments, product 500 includes a loosely compacted cellulosic fibrous batt, and integral therewith, a continuous paper-like densified, cellulosic fibrous layer 504. The batt of absorbent structure 500 is formed of loosely compacted short cellulose fibers, such as wood pulp fibers, or cotton linters, or mixtures thereof, which are primarily held together by interfiber bonds requiring no added adhesive, as is known in the art. This batt is a low bulk density coherent web of loosely compacted cellulose fibers preferably comminuted wood pulp fibers in the form of so-called "fluff".

Product 500 is subjected to embossing pressure subsequent to the formation of the densified layer or skin 504 by a ribbed embossing roll, such as that shown at 35 in FIG. 9, to form a plurality of spaced, parallel thickened densified lines 506. However, unlike the previous embodiments, lines 506 are not coherent and unitary and instead, the moisture application and embossing forces are coordinated and controlled so that lines 506 have substantially fiber-free regions 508 therein, which may be termed "voids", "pores", "cells", "gaps", or "pockets".

As is evident by comparing FIGS. 20 and 21, lines 506 include a plurality of vertically spaced fiber-free regions 508 which are generally lens-shaped, or biconvex in transverse cross section (FIG. 20) and which are elongated in the direction of the lines (FIG. 21). The regions 508 are separated from one another by spaced fibrous strata 510 which are generally parallel with one another and with the opposite major faces of the product 500, as can be best seen in FIG. 21. The strata 510 are of random or non-uniform length and merge together (and with the continuous densified portion 504) at longitudinally spaced locations 512 to completely enclose regions 508. As is also evident from FIGS. 20 and 21, regions 508 are of non-uniform cross-sectional dimension and length.

While it is not intended to be limited to any particular theory, it is believed that under certain selected moisture and pressure conditions (which may vary for different pulp fibers), as the batt dries subsequent to the embossing step the hydrogen bonds which may have previously caused the lines to be cohesive or unitary begin to weaken due to the inherent recovery force of the fibrous mass, which cause the lines to separate as shown in FIGS. 20 and 21.

Structures such as shown in FIGS. 20 and 21 may also be produced by mechanically working a product having coherent or unitary lines, as by subjecting the product to bending and/or twisting forces, which cause certain of the hydrogen bonds to rupture thus producing a product having thickened lines with dense fibrous strata surrounding substantially fiber-free regions.

While each of the strata 510 may have a density that is greater than the fibrous regions 514 at opposite sides of the lines 506, the density of the strata 510 is not necessarily uniform and the strata in the mid-portion of the batt may be less dense than the strata outwardly thereof.

It will be appreciated that with thickened densified lines having separated planes or strata of densified material, fluid will flow in the direction of the lines at a rapid linear rate, although the volumetric flow rate within each of the planes of densified material will, of necessity, be low because of the limited cross-sectional area in each plane. However, the voids or pores between the planes of densified material act as reservoirs into which excess liquid carried in the planes can be spilled, thereby providing an increased volumetric storage capacity and an increased volumetric carrying capacity, as compared to a cohesive or unitary line containing the same total amount of fibers.

Referring now to FIGS. 22–26, the graphs of these views illustrate the process conditions that are applicable to obtain thickened lines with or without voids for an NBF Kraft pulp available from Weyerhauser Company and which consists of approximately 80% Loblolly pine, 20% Ponderosa pine and traces of slash pine and which has a fiber classification of 54.6% + 12 mesh, 23.5% + 28 mesh, 10.8% + 48mesh, 4.5% + 100 mesh, and 6.6% − 100 mesh. The pulp board was ground in a Fitz mill and processed as shown in FIG. 9. The embossing roll was floatingly mounted and loaded with a dead weight, and the embossing roll was formed of metal with a main diameter of 2.81 inches and a ring diameter of 2.94 inches, with a ring width of 0.125 inches. The back-up roll was formed of metal and was fixedly mounted relative to the embossing roll, with the backing roll having a diameter of 3,825 inches. For the purposes of FIGS. 22–25, void areas are those areas in excess of 0.05 m.m.

Referring first to FIG. 22, which is a plot with moisture add-on in increasing amounts as the abscissa and embossing force in increasing amounts as the ordinate, it should be noted that at those moisture and pressure conditions above line "A", all of the thickened densified lines will be coherent and unitary, while at those moisture and pressure conditions below line "A", the thickened densified lines will contain a percentage of regions substantially devoid of fibers. At increasing distances below line A, the percentage of samples having void regions increases, and above line B approximately 10% of the samples had void regions, while above line C approximately 20% of the samples had void regions. The samples that are graphed in FIG. 22 were taken immediately after production and at relatively low production speeds. Each sample below line A in FIG. 22 was observed to have void regions at given longitudinal sections thereof, and it is believed that void regions in up to 100% of the length of the densified lines of a given sample can be produced under certain process conditions including high-speed production runs where the time under pressure is short and the fibers have significant elastic recovery.

Turning now to FIGS. 23–26, which are plots with density in increasing amounts as the abscissa and embossing force in increasing amounts as the ordinate, the solid lines represent measurements that include the void regions, while the dotted lines represent measurements that exclude the void regions. The solid and dotted lines in each view represent [for moisture add-on per panel (10¾ inches × 14¾ inches) of zero, 1 gram, 2 grams and 4 grams, respectively] lines of demarcation between those samples wherein the thickened densified lines had voids and those samples wherein the thickened densified lines were solid or coherent. In connection with FIG. 23 is should be noted that the fibers are not bone dry and that there is enough moisture in the ambient atmosphere to enable some hydrogen bonding to take place.

While processing conditions for obtaining structures as shown in FIGS. 20 and 21 have been given for only one specific type of fiber, it will be apparent to those skilled in the art that similar results can be obtained for different types of fibers, and that the specific reference to only one type of fibers is in no way meant to be limitative upon the invention.

It will be understood by those skilled in the art that variations and modifications of the specific embodiments described above may be employed without departing from the scope of the invention as defined in the appended claims.

What is claimed is:

1. An absorbent fibrous structure having a length dimension greater than its width dimension and comprising: a highly porous, loosely compacted cellulosic fibrous batt having oppositely facing major surfaces; a paper-like, densified compacted cellulosic fibrous layer integral with said loosely compacted batt and extending continuously over substantially the entire area of one of the major surfaces thereof, said densified layer being of substantially uniform thickness and merging with the loosely compacted portion of said batt at a generally planar interface; said densified layer including spaced, relatively narrow zones of densified compacted cellulosic fibers of greater thickness dimension than the uniform thickness portion of said densified layer and projecting beyond the interface between said loosely compacted batt and said densified layer, said zones being generally parallel with one another and extending lengthwise with respect to said structure, said zones being integral with the uniform thickness portion of said densified layer and extending through the entire cross-sectional thickness of the batt to provide a three-dimensional shear resistance whereby the strength and cohesiveness of the absorbent structure is increased; and the surface of said batt opposite to said densified layer being recessed inwardly toward said densified layer in the area of each of said zones to provide a cushioning effect.

2. An absorbent fibrous structure as set forth in claim 1 wherein said narrow zones extend from end to end of said product.

3. An absorbent structure as set forth in claim 1 including additional zones of greater thickness dimension than said densified layer extending transversely relative to said zones near the end edges of said batt.

4. An absorbent fibrous structure as set forth in claim 1 wherein the batt has a central portion of greater thickness dimension to provide a stepped construction including batt side portions of reduced thickness.

5. An absorbent fibrous structure as set forth in claim 1 wherein the continuous densified layer is thicker in the central region of the batt.

6. An absorbent fibrous structure as set forth in claim 1 wherein each zone includes a plurality of strips of greater thickness dimension separated by areas of substantially the same thickness as said layer.

7. An absorbent fibrous structure as set forth in claim 6 wherein the strips are substantially longer than the areas therebetween.

8. An absorbent fibrous structure as set forth in claim 6 wherein the strips in each zone are staggered relative to strips in adjacent zones.

9. An absorbent fibrous structure as set forth in claim 1 wherein the zones of greater thickness dimension are coherent and unitary.

10. An absorbent fibrous structure as set forth in claim 1 wherein the zones of greater thickness dimension include spaced fibrous strata surrounding substantially fiber free voids.

11. An absorbent fibrous structure as set forth in claim 10 wherein said voids are substantially biconvex in transverse cross section.

12. An absorbent fibrous structure as set forth in claim 10 wherein said zones of greater thickness dimension include a plurality of vertically spaced voids separated by one another by vertically spaced strata.

13. An absorbent fibrous structure as set forth in claim 10 wherein spaced portions of said strata merge with one another.

14. An absorbent fibrous structure as set forth in claim 10 wherein said strata extend in the direction of said zones.

15. An absorbent fibrous structure as set forth in claim 14 wherein said strata extend generally parallel to the major faces of said structure.

16. An absorbent fibrous structure as set forth in claim 1 wherein the uniform thickness portion of said densified layer and said zones of greater thickness dimension are retained in the compacted state solely by hydrogen bonds.

17. An absorbent fibrous structure as set forth in claim 1 wherein said zones of greater thickness dimension are generally rectilinear.

* * * * *